US00PP37048P2

(12) United States Plant Patent
van Swieten

(10) Patent No.: US PP37,048 P2
(45) Date of Patent: Oct. 21, 2025

(54) ***PHALAENOPSIS* PLANT NAMED 'PHA663401'**

(50) Latin Name: *Phalaenopsis hybrida*
Varietal Denomination: PHA663401

(71) Applicant: ANTHURA B.V., Bleiswijk (NL)

(72) Inventor: Martinus Nicolaas Gerardus van Swieten, Utrecht (NL)

(73) Assignee: ANTHURA B.V., Bleiswijk (NL)

( * ) Notice: Subject to any disclaimer, the term of this patent is extended or adjusted under 35 U.S.C. 154(b) by 0 days.

(21) Appl. No.: 19/017,724

(22) Filed: Jan. 12, 2025

(51) Int. Cl.
*A01H 5/02* (2018.01)
*A01H 6/62* (2018.01)

(52) U.S. Cl.
USPC ..... Plt./311

(58) Field of Classification Search
USPC ..... Plt./311
See application file for complete search history.

*Primary Examiner* — Susan McCormick Ewoldt
(74) *Attorney, Agent, or Firm* — C. Anne Whealy

(57) ABSTRACT

A new and distinct cultivar of *Phalaenopsis* plant named 'PHA663401', characterized by its upright and relatively compact plant habit; relatively moderately vigorous growth habit and moderate growth rate; strong flowering stems; healthy and sturdy leaves; freely flowering habit with typically two inflorescences developing per plant, each inflorescence with numerous flowers; white-colored flowers with mostly white-colored labella; and good postproduction longevity.

2 Drawing Sheets

Figure 1:
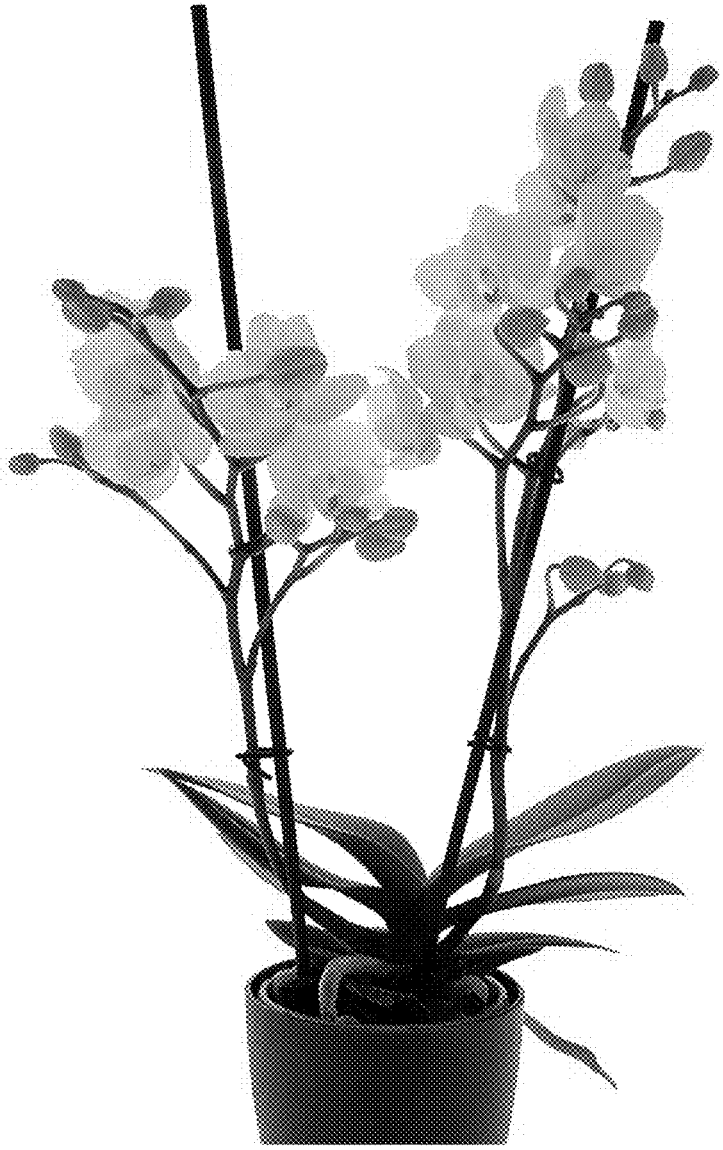

Botanical designation: *Phalaenopsis hybrida.*
Cultivar denomination: 'PHA663401'.

STATEMENT REGARDING PRIOR DISCLOSURES BY INVENTOR and APPLICANT/ASSIGNEE

A European Community Plant Breeder's Rights application for the instant plant was filed by the Applicant/Assignee of the instant application, Anthura B.V. of Bleiswijk, The Netherlands on Aug. 14, 2024, application number 2024/1896, and published on Oct. 15, 2024. Foreign priority is not claimed to this application.

BACKGROUND OF THE INVENTION

The present invention relates to a new and distinct cultivar of *Phalaenopsis* plant, botanically known as *Phalaenopsis hybrida*, commonly referred to as a *Phalaenopsis* or Moth Orchid and hereinafter referred to by the name 'PHA663401'.

The new *Phalaenopsis* plant is a product of a planned breeding program conducted by the Inventor in Bleiswijk, The Netherlands. The objective of the breeding program is to develop new compact and freely flowering *Phalaenopsis* plants with flowers with unique and attractive patterns and coloration.

The new *Phalaenopsis* plant originated from a cross-pollination in July 2017 in Bleiswijk, The Netherlands of *Phalaenopsis hybrida* 'PHALFLABAL', disclosed in U.S. Plant Pat. No. 27,458, as the female, or seed, parent with a proprietary selection of *Phalaenopsis hybrida* identified as code number 08-000001-9277, not patented, as the male, or pollen, parent. The new *Phalaenopsis* plant was discovered and selected by the Inventor as a single flowering plant from within the progeny of the stated cross-pollination grown in a controlled greenhouse environment in Bleiswijk, The Netherlands in March 2020.

Asexual reproduction of the new *Phalaenopsis* plant by in vitro meristem propagation in a controlled environment in Bleiswijk, The Netherlands since March 2020 has shown that the unique features of this new *Phalaenopsis* plant are stable and reproduced true to type in successive generations.

SUMMARY OF THE INVENTION

Plants of the new *Phalaenopsis* have not been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of 'PHA663401'. These characteristics in combination distinguish 'PHA663401' as a new and distinct *Phalaenopsis* plant:

1. Upright and relatively compact plant habit.
2. Relatively moderately vigorous growth habit and moderate growth rate.
3. Strong flowering stems.
4. Healthy and sturdy leaves.
5. Freely flowering habit with typically two inflorescences developing per plant, each inflorescence with numerous flowers.
6. White-colored flowers with mostly white-colored labella.
7. Good postproduction longevity.

Plants of the new *Phalaenopsis* can be compared to plants of the female parent, 'PHALFLABAL'. Plants of the new *Phalaenopsis* differ primarily from plants of 'PHALFLABAL' in the following characteristics:

1. Flowers of plants of the new *Phalaenopsis* are mostly flat to slightly concave whereas flowers of plants of 'PHALFLABAL' are convex.
2. Dorsal sepals of plants of the new *Phalaenopsis* are broader than dorsal sepals of plants of 'PHALFLABAL'.

Plants of the new *Phalaenopsis* can be compared to plants of the male parent selection. Plants of the new *Phalaenopsis* differ primarily from plants of the male parent selection in the following characteristics:

1. Plants of the new *Phalaenopsis* have longer leaves than plants of the male parent selection.
2. The labella lateral lobes of plants of the new *Phalaenopsis* are not as inwardly curved as the labella lateral lobes of plants of the male parent selection.

Plants of the new *Phalaenopsis* can be compared to plants of *Phalaenopsis hybrida* 'PHALGOPWIJ', disclosed in U.S. Plant Pat. No. 31,805. In side-by-side comparisons, plants of the new *Phalaenopsis* differ primarily from plants of 'PHALGOPWIJ' in the following characteristics:

1. Leaf aspect of plants of the new *Phalaenopsis* is semi-erect to horizontal whereas leaf aspect of plants of 'PHALGOPWIJ' is horizontal to semi-drooping.
2. The labella lateral lobes of plants of the new *Phalaenopsis* are more inwardly curved than the labella lateral lobes of plants of 'PHALGOPWIJ'.

BRIEF DESCRIPTION OF THE PHOTOGRAPHS

The accompanying photographs illustrate the overall appearance of the new *Phalaenopsis* plant showing the colors as true as it is reasonably possible to obtain in colored reproductions of this type. Colors in the photographs may differ slightly from the color values cited in the detailed botanical description which accurately describe the colors of the new *Phalaenopsis* plant.

The photograph on the first sheet (FIG. 1) is a side perspective view of a typical flowering plant of 'PHA663401' grown in a container.

Figure 2:
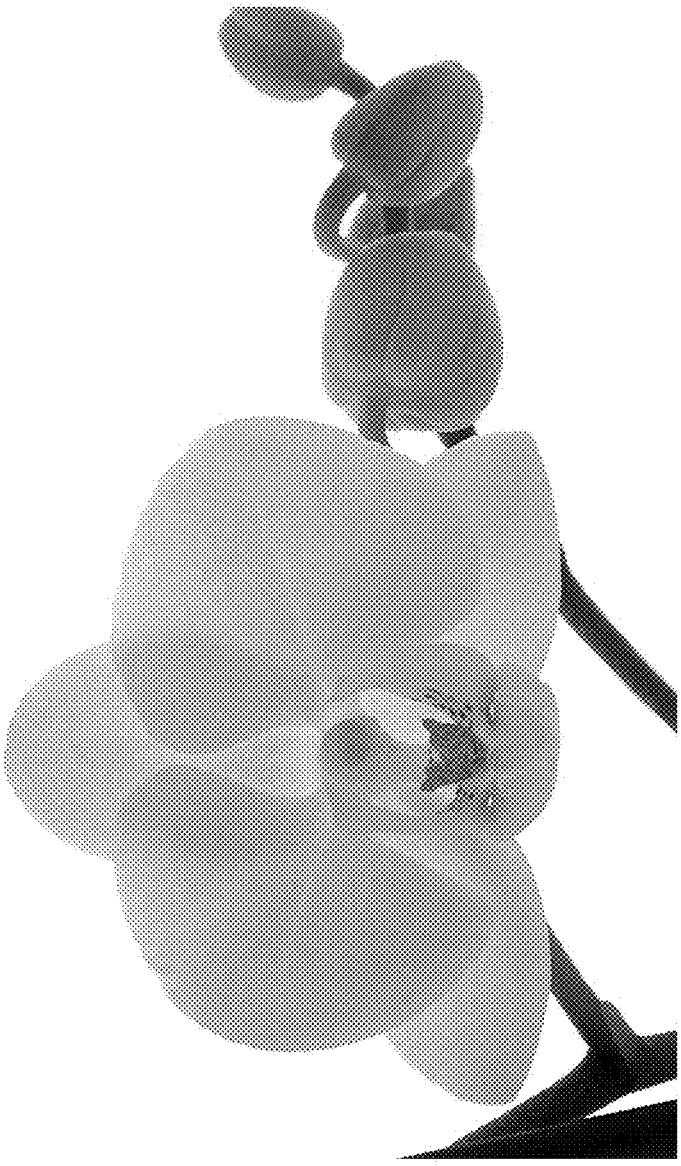

The photograph on the second sheet (FIG. 2) is a close-up view of a typical flowering stem of 'PHA663401'.

DETAILED BOTANICAL DESCRIPTION

The aforementioned photographs and following observations and measurements describe plants grown during the autumn in 9-cm containers in a glass-covered greenhouse in Bleiswijk, The Netherlands and grown under cultural practices typically used in commercial *Phalaenopsis* production. Plants were 16 months old when the photographs and description were taken. During the first 13 months of production of the plants, day and night temperatures averaged 28.5° C., and during the last three months of production of the plants, day and night temperatures averaged 20° C. Throughout the production of the plants, light levels ranged from 100 μmol to 180 μmol. In the following description, color references are made to The Royal Horticultural Society Colour Chart, 2015 Edition, except where general terms of ordinary dictionary significance are used.

Botanical classification: *Phalaenopsis hybrida* 'PHA663401'.

Parentage:

*Female, or seed, parent.*—*Phalaenopsis hybrida* 'PHALFLABAL', disclosed in U.S. Plant Pat. No. 27,458.

*Male, or pollen, parent.*—Proprietary selection of *Phalaenopsis hybrida* identified as code number 08-000001-9277, not patented.

Propagation:

*Type.*—By in vitro meristem propagation.

*Time to initiate roots, summer and winter.*—About two weeks at temperatures about 28° C. to 30° C.

*Time to produce a rooted young plant, summer and winter.*—About 20 to 25 weeks at temperatures about 28° C. to 30° C.

*Root description.*—Thick, fibrous; typically light green in color; actual color of the roots is dependent on substrate composition, water quality, fertilizer, substrate temperature and age of roots.

*Rooting habit.*—Freely branching; medium density.

Plant description:

*Plant form and growth habit.*—Herbaceous epiphyte; upright and relatively compact plant habit with typically two inflorescences developing per plant, each inflorescence with numerous flowers; monopodial; relatively moderately vigorous growth habit and moderate growth rate.

*Plant height, substrate level to top of foliar plane.*—About 8.2 cm.

*Plant height, substrate level to top of floral plane.*—About 31 cm.

*Plant diameter or spread.*—About 21.1 cm.

Leaf description:

*Arrangement and quantity.*—Distichous, simple; sessile; about three to seven fully-developed leaves per plant.

*Length.*—About 12.8 cm.

*Width.*—About 6 cm.

*Aspect.*—Semi-erect to horizontal.

*Shape.*—Obovate-elliptic to broadly elliptic; slightly carinate.

*Apex.*—Unequal obtuse.

*Base.*—Sheathing. Sheath length: About 1.5 cm. Sheath width: About 1.2 cm. Sheath color: Close to 143C; towards the margins, close to 143A.

*Margin.*—Entire; not undulate.

*Texture and luster, upper surface.*—Smooth, glabrous; slightly glossy.

*Texture and luster, lower surface.*—Smooth, glabrous; slightly to moderately glossy.

*Venation pattern.*—Camptodromous.

*Color.*—Developing leaves, upper surface: Close to a blend of NN137B and 146A; narrow marginal edges, close to 145A and 145B. Developing leaves, lower surface: Close to 144A; narrow marginal edges, close to 145A and 145B. Fully expanded leaves, upper surface: Close to NN137B; narrow marginal edges, close to 145A; venation, close to NN137A. Fully expanded leaves, lower surface: Close to 146B; towards the margins and apex, close to 147A; narrow marginal edges, close to 145A; venation, close to 143A.

Inflorescence description:

*Appearance and flowering habit.*—Showy zygomorphic flowers arranged on axillary simple or branched racemes; typically two inflorescences develop per plant; each inflorescence with about 24flowers; flowers face outwardly on upright to outwardly arching inflorescences supported by upright peduncles; flowers with three petals, two lateral petals and one center petal transformed into a labellum and three sepals.

*Fragrance*.—None detected.

*Time to flower*.—Plants begin flowering about four months after planting; plants flower naturally during the winter into the spring.

*Flower longevity*.—Long flowering period, individual inflorescences maintain good substance for about 15 weeks on the plant; flowers not persistent.

*Inflorescence length* (*lowermost flower to inflorescence apex*).—About 22 cm.

*Inflorescence width*.—About 15.4 cm.

*Flower buds*.—Height: About 1.5 cm. Diameter: About 1.2 cm by 1.4 cm. Shape: Broadly ovate. Color: Close to 150D; towards the apex, close to 150C.

*Flower size*.—About 3.75 cm (vertical) by 4.8 cm (horizontal).

*Flower depth*.—About 2.4 cm.

*Petals, quantity and arrangement*.—Three, two lateral petals and one center petal transformed into a labellum.

*Lateral petals*.—Length: About 2.6 cm. Width: About 3 cm. Shape: Broadly deltoid-reniform to broadly deltoid-ovate. Apex: Obtuse. Margin: Entire; not undulate. Texture and luster, upper and lower surfaces: Smooth, glabrous, moderately velvety; matte. Color: When opening, upper and lower surfaces: Close to NN155D. Fully opened, upper and lower surfaces: Close to NN155D; venation, close to NN155D; color does not change with subsequent development.

*Labella*.—Appearance: Three-parted with two lateral lobes and a central lobe; overall shape, reniform. Length, lateral lobes: About 1.6 cm. Width, lateral lobes: About 1.2 cm. Length, central lobe: About 1.5 cm. Width, central lobe: About 4 mm to 13 mm. Length, cirrhose tips: About 6 mm. Shape, lateral lobes: Obovate. Shape, central lobe: Ovate with a slightly elongated apex. Apex, lateral lobes: Obtuse. Apex, central lobe: Cleft with two upwardly and backwardly curled cirrhose tips. Margins, lateral and central lobes: Entire. Texture and luster, lateral and central lobes, upper and lower surfaces: Smooth, glabrous, moderately velvety; matte. Callosities: Located at the base of the labellum and attachment point of the lateral petals; about 3.5 mm in length, about 4.5 mm in width and about 4 mm in height. Color: When opening, upper surface: Lateral lobes: Close to NN155D; lower margins, close to 154D; at the base, axial stripes and dots, close to 175A. Central lobe: Close to NN155D; distal margins, close to 150C; at the base, close to NN155D with radial stripes, close to 176D; cirrhose tips, close to NN155D. Callosities: Close to 145D; distally, close to 9A and 9B with fine dots, close to 176D; center, close to 4C. When opening, lower surface: Lateral lobes: Close to NN155D; lower margins, close to 154D. Central lobe: Close to NN155D and 155C; distal margins, close to 150C; at the base, close to 156D; cirrhose tips, close to NN155D. Fully opened, upper surface: Lateral lobes: Close to NN155D; lower margins, close to 2B; at the base, axial stripes and dots, close to 178D. Central lobe: Close to NN155D; distal margins, close to 154D; at the base, close to NN155D with radial stripes, close to 178C; cirrhose tips, close to NN155D. Callosities: Close to 154D; distally, close to 12A with fine dots, close to 176D; center, close to 9C. Fully opened, lower surface: Lateral lobes: Close to NN155D; lower margins, close to 154D. Central lobe: Close to NN155C to NN155D; distal margins, close to 154D; at the base, close to 156D; cirrhose tips, close to NN155C to NN155D.

*Sepals*.—Quantity and arrangement: Three, one upper dorsal sepal and two lower lateral sepals. Length, dorsal sepal: About 2.5 cm. Width, dorsal sepal: About 1.8 cm. Length, lateral sepals: About 2.6 cm. Width, lateral sepals: About 1.7 cm. Shape, dorsal sepal: Elliptic to close to oblong. Shape, lateral sepals: Ovate. Apex, dorsal sepal: Obtuse to shallow and minutely emarginate. Apex, lateral sepals: Acute. Base, dorsal and lateral sepals: Truncate. Margins, dorsal and lateral sepals: Entire; not undulate. Texture and luster, dorsal and lateral sepals, upper and lower surfaces: Smooth, glabrous, moderately velvety; matte. Color, dorsal sepal: When opening, upper surface: Close to 155C; towards the apex and margins, close to NN155D. When opening, lower surface: Close to 145D faintly tinged with close to 76C; towards the apex and margins, close to NN155B. Fully opened, upper surface: Close to NN155B; towards the apex and margins, close to NN155D; venation, similar to lamina color. Fully opened, lower surface: Close to 155A faintly tinged with close to 76C; towards the apex and margins, close to NN155C; venation, similar to lamina color. Color, lateral sepals: When opening, upper surface: Distally, close to 155C and proximally, close to 157D; towards the base, close to 145C and 145D. When opening, lower surface: Distally, close to 155C and proximally, close to 145C and 145D. Fully opened, upper surface: Distally, close to NN155C and proximally, close to 157D; towards the base, close to 145C and 145D; venation, similar to lamina color. Fully opened, lower surface: Distally, close to NN155C and proximally, close to 155C; towards the base, close to 145C and 145D; main vein, close to 145C and 145D; lateral venation, similar to lamina color.

*Peduncles*.—Length: About 29.1 cm. Diameter: About 4 mm. Strength: Strong. Aspect: Upright to outwardly arching. Texture and luster: Smooth, glabrous; matte. Color: Close to 148A densely covered with fine dots, close to 145B and N199A.

*Pedicels*.—Length: About 3.25 cm. Diameter: About 2.5 mm. Strength: Moderately strong. Aspect: About 60° from peduncle axis. Texture and luster: Smooth, glabrous; matte. Color: Close to 145B and 145C; distal end, close to 159D faintly tinged with close to 69A; proximal end, close to 146A.

*Reproductive organs*.—Androecium: Column length: About 7 mm. Column width: About 4.5 mm. Column color: Close to NN155C. Pollinia quantity: Two. Pollinia diameter (per two pollinia): About 2 mm. Pollinia color: Close to 21A. Gynoecium: Stigma length: About 3 mm. Stigma width: About 4 mm. Stigma shape: Reniform. Stigma color: Close to 155C. Ovary length: About 8 mm. Ovary diameter: About 1 mm. Ovary color: Close to 146D. Seeds and fruits: To date, seed and fruit development have not been observed on plants of the new *Phalaenopsis*.

Pathogen & pest resistance: To date, plants of the new *Phalaenopsis* have not been shown to be resistant to pathogens and pests common to *Phalaenopsis* plants.

Temperature tolerance: Plants of the new *Phalaenopsis* have been observed to tolerate high temperatures about 40° C. and are suitable for USDA Hardiness Zones 10 to 12.

It is claimed:

1. A new and distinct *Phalaenopsis* plant named 'PHA663401' as herein illustrated and described.

* * * * *